(12) United States Patent
Wall et al.

(10) Patent No.: US 7,071,204 B2
(45) Date of Patent: Jul. 4, 2006

(54) CAMPTOTHECIN ANALOGS HAVING AN E-RING KETONE

(75) Inventors: Monroe E. Wall, deceased, late of Portland, OR (US); by Michael A. Wall, legal representative, Portland, OR (US); Mansukh C. Wani, Durham, NC (US); Govindarajan Manikumar, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 60 days.

(21) Appl. No.: 10/608,207

(22) Filed: Jun. 30, 2003

(65) Prior Publication Data

US 2004/0266804 A1 Dec. 30, 2004

(51) Int. Cl.
*A61K 31/407* (2006.01)
*C07D 487/02* (2006.01)
*C07D 487/14* (2006.01)

(52) U.S. Cl. .......................................... 514/283; 546/58
(58) Field of Classification Search ................... 546/58; 514/283
See application file for complete search history.

(56) References Cited

U.S. PATENT DOCUMENTS

| | | | |
|---|---|---|---|
| 4,894,456 A | 1/1990 | Wall et al. | |
| 4,981,968 A | 1/1991 | Wall et al. | |
| 5,049,668 A | 9/1991 | Wall et al. | |
| 5,053,512 A | 10/1991 | Wani et al. | |
| 5,106,742 A | 4/1992 | Wall et al. | |
| 5,122,526 A | 6/1992 | Wall et al. | |
| 5,122,606 A | 6/1992 | Wani et al. | |
| 5,180,722 A | 1/1993 | Wall et al. | |
| 5,227,380 A | 7/1993 | Wall et al. | |
| 5,244,903 A | 9/1993 | Wall et al. | |
| 5,340,817 A | 8/1994 | Wall et al. | |
| 5,364,858 A | 11/1994 | Wall et al. | |
| 5,401,747 A | 3/1995 | Wall et al. | |
| 5,496,830 A | 3/1996 | Shapiro et al. | |
| 5,614,529 A | 3/1997 | Wall et al. | |
| 5,646,159 A | 7/1997 | Wall et al. | |
| 5,932,588 A | 8/1999 | Wall et al. | |
| 5,985,888 A | 11/1999 | Wall et al. | |
| 6,043,367 A * | 3/2000 | Roffler et al. | ............... 546/48 |
| 6,268,375 B1 | 7/2001 | Wall et al. | |
| 6,288,072 B1 | 9/2001 | Wall et al. | |
| 6,509,345 B1 * | 1/2003 | Lavielle et al. | ............. 514/283 |
| 6,699,876 B1 * | 3/2004 | Lavielle et al. | ............. 514/283 |

FOREIGN PATENT DOCUMENTS

EP     1101765     *   5/2001

OTHER PUBLICATIONS

International Search Report/PCTUS04/17436, (International filing date, Jun. 30, 2004).
Written Opinion of the International Searching Authority/PCT/US04/17436.

* cited by examiner

*Primary Examiner*—Rita Desai
(74) *Attorney, Agent, or Firm*—Oblon, Spivak, McClelland, Maier & Neustadt, P.C.

(57) ABSTRACT

Camptothecin analogs having an E-ring ketone are effective anti tumor compounds. These compounds inhibit the enzyme topoisomerase I and may alkylate DNA of the associated topoisomerase I DNA cleavable complex.

16 Claims, 3 Drawing Sheets

CAMPTOTHECIN ANALOGS HAVING AN E-RING KETONE

BACKGROUND OF THE INVENTION

1. Field of the Invention

This invention relates to camptothecin analogs having an E-ring ketone which inhibit the enzyme topoisomerase I and have anticancer activity. This invention is also related to the treatment of tumors in animals with camptothecin analogs

2. Background of the Invention

Camptothecin (CPT) is a naturally occurring cytotoxic alkaloid which is known to inhibit the enzyme topoisomerase I and is a potent anti tumor agent. Camptothecin compounds have the general ring structure shown below.

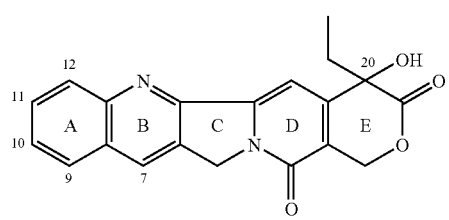

Camptothecin was isolated from the wood and bark of *Camptotheca acuminata* by Wall et al. (Wall et al., 1966, J. Am. Chem. Soc., 88:3888). It has been shown that if the E-ring α-hydroxy lactone functions are altered or removed, that the resulting compounds have no activity regarding topoisomerase I inhibition or inhibition of cancer cells. (Wall, Plant Antitumor Agents. V. Alkaloids with Antitumor Activity Symposiumsberichtes, pp. 77 87, 4. Internationales Symposium, Biochemie und Physiologie der Alkaloide, Halle (Saale) 25. Bis 28. June, 1969, edited by K. Mothes, K. Schreiber, and H. R. Schutte, Akademie Verlag, Berlin, 1969; and Nicholas et al, J. Med. Chem., 33, 972 (1990).)

Another process that affects all camptothecin compounds is that at an alkaline pH, as low as 7.5 or higher, the lactone-ring is readily hydrolyzed to give an E-ring opened carboxylate product. This compound is much less active in the above mentioned activities.

The cytotoxic activity of camptothecin compounds is believed to arise from the ability of these compounds to inhibit both DNA and RNA synthesis and to cause reversible fragmentation of DNA in mammalian cells. Topoisomerase I relaxes both positively and negatively supercoiled DNA and has been implicated in various DNA transactions such as replication, transcription and recombination. The enzyme mechanism is believed to involve a transient breakage of one of the two DNA strands and the formation of a reversible covalent topoisomerase I enzyme DNA complex. Camptothecin interferes with the DNA breakage reunion reaction by reversibly trapping the enzyme DNA intermediate termed the "cleavable complex". The cleavable complex assay is a standard test for determining the cytotoxic activity of camptothecin compounds. The high levels of topoisomerase I in several types of human cancer and the low levels in correspondingly normal tissue provide the basis for tumor treatment with biologically active camptothecin analogs.

U.S. Pat. No. 4,894,456 describes methods of synthesizing camptothecin compounds which act as inhibitors of topoisomerase I and are effective in the treatment of leukemia (L 1210). U.S. Pat. No. 5,225,404 discloses methods of treating colon tumors with camptothecin compounds.

Numerous camptothecin compounds and their use as inhibitors of topoisomerase I are reported by U.S. Pat. No. 5,053,512; U.S. Pat. No. 4,981,968; U.S. Pat. No. 5,049,668; U.S. Pat. No. 5,106,742; U.S. Pat. No. 5,180,722; U.S. Pat. No. 5,244,903; U.S. Pat. No. 5,227,380; U.S. Pat. No. 5,122,606; U.S. Pat. No. 5,122,526; and U.S. Pat. No. 5,340,817.

U.S. Pat. No. 4,943,579 discloses the esterification of the hydroxyl group at the 20 position of camptothecin to form several prodrugs. This patent further discloses that the prodrugs are water soluble and are converted into the parent camptothecin compounds by hydrolysis.

Brangi et al., *Cancer Research*, 59, 5938 5946 Dec. 1, 1999, reports an investigation of Camptothecin resistance in cancer cells and reports the compound difluoro 10, 11 methylenedioxy 20(S) camptothecin.

A need continues to exist, however, for camptothecin analogs having improved stability under physiological conditions.

SUMMARY OF THE INVENTION

Accordingly, one object of the present invention is to provide a camptothecin analog having improved stability under physiological conditions.

Another object of the present invention is to provide a method of treating leukemia or solid tumors in a mammal in need thereof by administration of a camptothecin analogs.

Another object of the present invention is to provide a method of inhibiting the enzyme topoisomerase I and/or alkylating DNA of associated DNA topoisomerase I by contacting a DNA topoisomerase I complex with a camptothecin analog.

These and other objects of the present invention are made possible by a camptothecin analog having the structure:

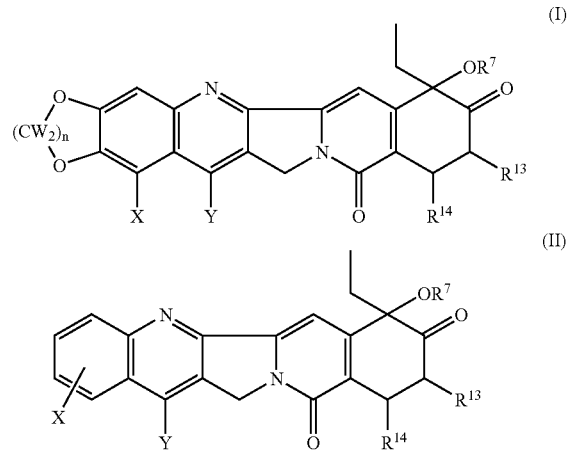

where

X and Y are each independently $NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, N($C_{1-6}$ alkyl)$_2$, CHO, $C_{1-8}$ alkyl, $N_3$, —Z—$(CH_2)_a$—N—$((CH_2)_b OH)_2$, wherein Z is selected from the group consisting of O, NH and S, and a and b are each independently an integer of 2 or 3, —Z—$(CH_2)_2$—N—$(C_{1-6}$ alkyl)$_2$ wherein Z is selected from the group consisting of O, NH and S, and a is an integer of 2 or 3, —$CH_2$-L, where L is halogen (F, Cl, Br, I), $^+N_2$, $^+(OR^1)_2$, $^+S(R^1)_2$, $^+N(R^1)_3$, $OC(O)R^1$, $OSO_2R^1$, $OSO_2CF_3$, $OSO_2C_4F_9$, $C_{1-6}$ alkyl-C(=O)—, $C_{4-18}$ aryl-C(=O)—, C—$_{1-6}$ alkyl, SO-2-, perfluoro $C_{1-6}$alkyl-$SO_2$— or $C_{4-18}$ aryl-$SO_2$—, (where each $R^1$ independently is $C_{1-6}$ alkyl, $C_{4-18}$ aryl or $C_{4-18}ArC_{1-6}$ alkyl); or —$CH_2NR^2R^3$, where (a) $R^2$ and $R^3$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxyl-$C_{1-6}$ alkyl, $C_{1-6}$ alkoxy-$C_{1-6}$ $COR^4$ where $R^4$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxyl-$C_{1-6}$ alkyl, $C_{1-6}$ alkoxy, or $C_{1-6}$ alkoxy-$C_{1-6}$ alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxyl-$C_{1-6}$ alkyl, $C_{1-6}$ alkoxy, $C_{1-6}$ alkoxy-$C_{1-6}$ alkyl and —$COR^6$ where $R^6$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxyl-$C_{1-6}$ alkyl, or $C_{1-6}$ alkoxy-$C_{1-6}$ alkyl groups;

$R^7$ is H, or $C(O)—(CH_2)_m—NR^8R^9$, where m is an integer of 1–6 or —$C(O)CHR^{10}NR^8R^9$, where $R^{10}$ is the side chain of one of the naturally occurring α-amino acids, $R^8$ and $R^9$ are, independently, hydrogen, $C_{1-8}$ alkyl or —$C(O)CHR^{11}NR^{12}R^{13}$, where $R^{11}$ is the side chain of one of the naturally occurring α-amino acids and $R^{12}$ and $R^{13}$ are each independently hydrogen or $C_{1-8}$ alkyl;

W is independently H or F, $R^{13}$ and $R^{14}$ are each H or combine to form a double bond; and n is an integer of 1 or 2, and salts thereof.

These compounds have the necessary α-hydroxy-ethyl substitutents at $C_{20}$ and a ketone in place of the lactone structure. Such a compound has a spatial orientation virtually identical with that of camptothecin, however it is much more stable than CPT under alkaline conditions.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1:
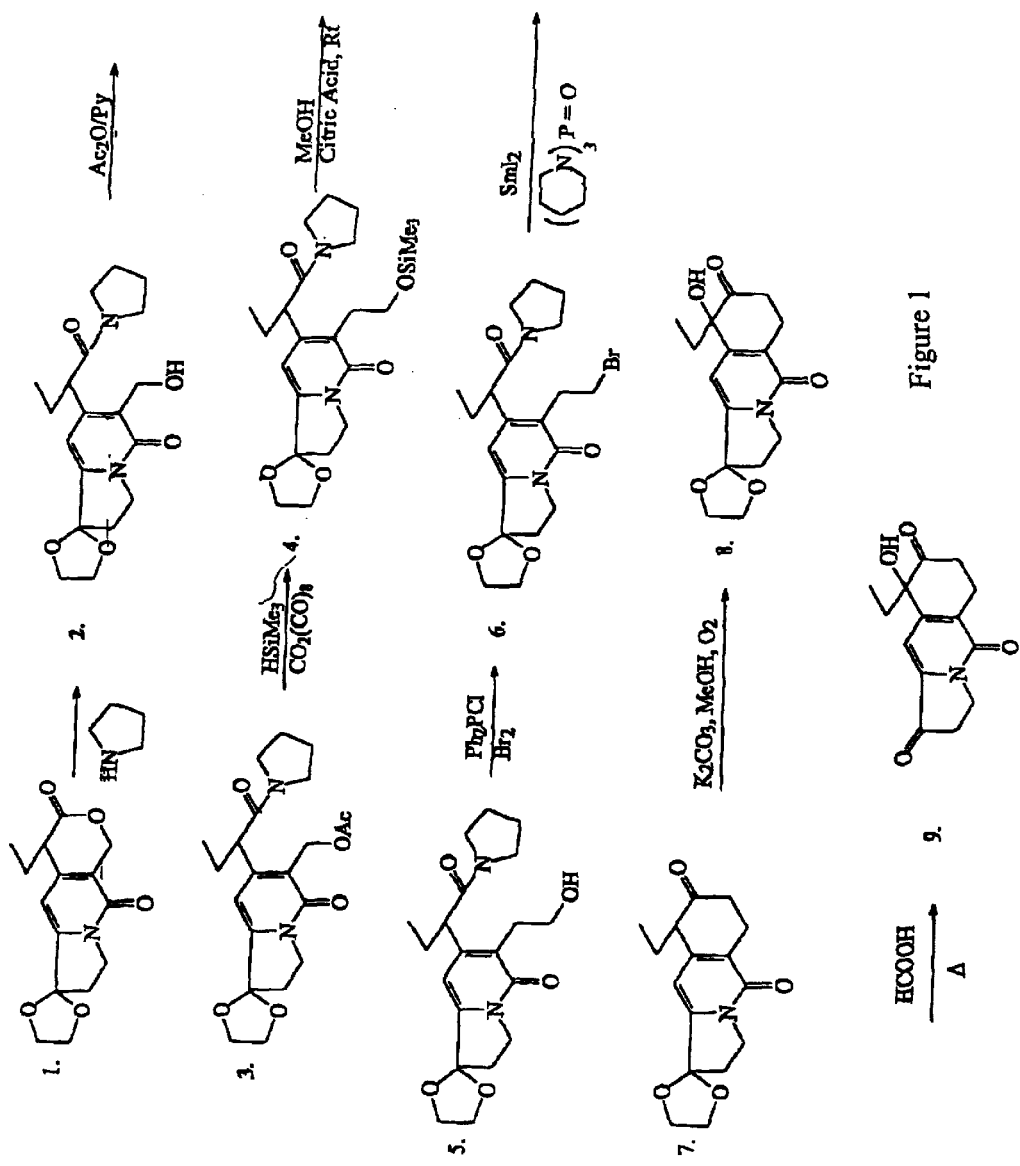
FIG. 1 illustrates the synthesis of a tricyclic ketone used to form the compound of the present invention.

DETAILED DESCRIPTION OF THE
PREFERRED EMBODIMENTS

Unless indicated to the contrary, the term "alkyl" as used herein means a straight chain or branched chain alkyl group with 1–30, preferably 1–18 carbon atoms, more preferably 1–8 carbon atoms, including methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. The term "alkyl" also includes $C_{3-30}$ cycloalkyl groups such as cyclopropyl, cyclopentyl, cyclohexyl, cycloheptyl and cyclooctyl groups.

Unless indicated to the contrary, the term "aryl" as used herein means a carbocyclic aromatic ring having 6–18 carbon atoms, preferably 6 10 carbon atoms in the aromatic ring structure. The aromatic rings may be substituted by one or more alkyl group, preferably alkyl groups having 1–10 carbon atoms. A particularly preferred aryl group is phenyl.

Unless indicated to the contrary, the term "aralkyl" as used herein means a straight chain or branched chain alkyl group as defined above for the term "alkyl" bonded to an aryl group as defined above for the term "aryl". Preferred aralkyl groups are benzyl, phenethyl, etc.

As used herein, the term "acyl" means formyloxy and acyl moieties derived from aromatic carboxylic acids, heterocyclic carboxylic acids, aralkyl carboxylic acids, as well as alkyl and aromatic sulfonic acids. The alkyl groups of these acyloxy moieties may be a straight chain or branched chain alkyl group with 1–7 carbon atoms. Additionally, the acyl moiety may contain one or more unsaturated carbon carbon bonds and may also carry one or more substituents such as halogen, amino and hydroxyl groups.

The camptothecin analogs of the present invention may bear a leaving group at one or more of the positions $C_7$ or $C_9$ of the camptothecin ring structure. More specifically, the leaving group is a group of the formula —$CH_2$-L, where L is a functional group which can be easily displaced, i.e. L is a good leaving group in nucleophilic substitution reactions. Suitable groups L include halogen (F, Cl, Br, I), $^+N_2$, $^+O(R^1)_2$, $^+S(R^1)_2$, $^+N(R^1)_3$, $OC(O)R^1$, $OSO_2R^1$, $OSO_2CF_3$, and $OSO_2C_4F_9$, $C_{1-6}$alkyl-C(=O)—, $C_{4-18}$aryl-C(=O)—, $C_{1-6}$ alkyl-$SO_2$—, perfluoro$C_{1-6}$ alkyl-$SO_2$— and $C_{4-18}$ aryl-$SO_2$-, (where each $R^1$ independently is $C_{1-6}$ alkyl, $C_{4-18}$ aryl or $C_{4-18}$ $ArC_{1-6}$ alkyl).

While not being bound by any particular theory, it is believed that nucleophilic groups on DNA displace leaving group L from the camptothecin analogs of the present invention resulting in alkylation of the DNA by the alkylating group of the camptothecin ring structure. Suitable nucleophilic groups present in DNA include the nucleophilic groups found in DNA bases adenine, guanine, thymine, and cytosine, such as $NH_2$, —NH— and =N— groups. When a camptothecin analog of the invention having a —$CH_2$-L group is contacted with DNA, nucleophilic displacement of leaving group L results in alkylation of the nucleic acid. The compounds of the present invention exhibit a novel anti tumor activity by alkylating DNA.

Camptothecin analogs have an asymmetric carbon atom at the 20-position making two enantiomeric forms, i.e., the (R) and the (S) configurations, possible. This invention includes each enantiomeric form individually, as well as combinations or mixtures of these forms. The invention also includes other forms of the camptothecin analogs including solvates, hydrates, polymorphs, salts, etc. Particularly preferred compounds are camptothecin derivatives having the (S) configuration at the 20-position.

In a preferred embodiment, X is $NO_2$, $NH_2$, H, F, Cl, Br, I, COOH, OH, O—$C_{1-6}$ alkyl, SH, S—$C_{1-6}$ alkyl, CN, $CH_2NH_2$, NH—$C_{1-6}$ alkyl, $CH_2NHC_{1-6}$ alkyl, $N(C_{1-6}$ alkyl$)_2$, $CH_2N(C_{1-6}$ alkyl$)_2$, O—$CH_2CH_2N(CH_2CH_2OH)_2$, NH—$CH_2CH_2N(CH_2CH_2OH)_2$, S—$CH_2CH_2N(CH_2CH_2OH)_2$, O—$CH_2CH_2CH_2N(CH_2CH_2OH)_2$, NH—$CH_2CH_2CH_2N(CH_2CH_2OH)_2$, S—$CH_2CH_2CH_2N(CH_2CH_2OH)_2$, O—$CH_2CH_2N(CH_2CH_2CH_2OH)_2$, NH—$CH_2CH_2N(CH_2CH_2CH_2OH)_2$, S—$CH_2CH_2N(CH_2CH_2CH_2OH)_2$, O—$CH_2CH_2CH_2N(CH_2CH_2CH_2OH_2)_2$, NH—$CH_2CH_2CH_2N(CH_2CH_2CH_2OH_2)_2$, S—$CH_2CH_2CH_2N(CH_2CH_2CH_2OH_2)_2$, O—$CH_2CH_2N$ (C$_{1-6}$ alkyl)$_2$, NH—CH$_2$CH$_2$N(C$_{1-6}$ alkyl)$_2$, S—CH$_2$CH$_2$N(C$_{1-6}$ alkyl)$_2$, O—CH$_2$CH$_2$N(C$_{1-6}$ alkyl)$_2$, NH—CH$_2$CH$_2$N(C$_{1-6}$ alkyl)$_2$, S—CH$_2$CH$_2$CH$_2$N(C$_{1-6}$ alkyl)$_2$, CHO, N$_2$, C$_{1-8}$ alkyl, CH$_2$-L where L is halogen (F, Cl, Br, I), $^+$N$_2$, $^+$O(R$^1$)$_2$ (where each R$^1$ independently is alkyl, aryl or aralkyl as defined above), $^+$S(R$^1$)$_2$, $^+$N(R$^1$)$_3$, OC(O)R$^1$, OSO$_2$R$^1$, OSO$_2$CF$_3$, OSO$_2$C$_4$F$_9$, C$_{1-6}$alkyl-C(=O)—, C$_{4-18}$aryl-C(=O)—, C$_{1-6}$alkyl-SO$_2$—, perfluoro C$_{1-6}$alkyl-SO$_2$— and C$_{4-18}$aryl-SO$_2$-.

In a preferred embodiment Y is H, C$_{1-8}$ alkyl, or CH$_2$NR$^2$R$^3$ where (a) R$^2$ and R$^3$ are, independently, hydrogen, C$_{1-6}$ alkyl, C$_{3-7}$ cycloalkyl, C$_{3-7}$ cycloalkyl-C$_{1-6}$ alkyl, C$_{2-6}$ alkenyl, hydroxyl-C$_{1-6}$ alkyl, C$_{1-6}$ alkoxy-C$_{1-6}$ COR$^4$ where R$^4$ is hydrogen, C$_{1-6}$ alkyl, perhalo C$_{1-6}$ alkyl, C$_{3-7}$ cycloalkyl, C$_{3-7}$ cycloalkyl-C$_{1-6}$ alkyl, C$_{2-6}$ alkenyl, hydroxyl-C$_{1-6}$ alkyl, C$_{1-6}$ alkoxy, C$_{1-6}$ alkoxy-C$_{1-6}$ alkyl, or (b) R$^2$ and R$^3$ taken together with the nitrogen atom to which they are attached form a saturated 3–7 membered heterocyclic ring which may contain a O, S or NR$^5$ group, where R$^5$ is hydrogen, C$_{1-6}$ alkyl, perhalo C$_{1-6}$ alkyl, aryl, aryl substituted with one or more groups selected from the group consisting of C$_{1-6}$ alkyl, halogen, nitro, amino, C$_{1-6}$ alkylamino, perhalo-C$_{1-6}$ alkyl, hydroxyl-C$_{1-6}$ alkyl, C$_{1-6}$ alkoxy, C$_{1-6}$-alkoxy-C$_{1-6}$ alkyl and —COR$^6$ where R$^6$ is hydrogen, C$_{1-6}$ alkyl perhalo-C$_{1-6}$ alkyl, C$_{1-6}$ alkoxy, aryl, and aryl substituted with one or more C$_{1-6}$ alkyl, perhalo-C$_{1-6}$ alkyl, hydroxyl-C$_{1-6}$ alkyl, or C$_{1-6}$ alkoxy-C$_{1-6}$ alkyl groups.

The group R$^7$ may be an ester of a naturally occurring or non naturally occurring amino acid such as an ester of glycine or β-alanine. In particular, the present invention is directed to camptothecin analogs where the group R$^7$ is C(O)—(CH$_2$)$_m$—NR$^8$R$^9$, where m is the integer 1, 2, 3, 4, 5 and 6 and R$^8$ and R$^9$ are each H.

Suitable side chains R$^{10}$ and R$^{11}$ appearing on the group R$^7$ are the side chains of the amino acids glycine, α-alanine, β-alanine, valine, leucine, isoleucine, phenylalanine, tyrosine, tryptophan, lysine, arginine, histidine, aspartate, glutamate, asparagine, glutamine, cysteine and methionine. Moreover, the group R$^7$, may comprise two amino acid units linked by a peptide linkage. In particular the group R$^7$ may comprise a β-alanine group linked to a lysine of the structure

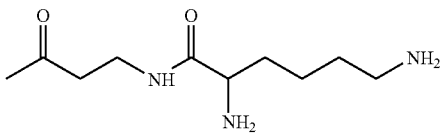

Moreover, the group R$^7$ may provide basis for the formation of a mono or di salts, via the free amine groups, such as a hydrochloride or dihydrochloride.

A synthon for attaching such a group to a terminal hydroxyl group is described by Hudkins et al. *Bioorg. Med. Chem. Lett*, 8 (1998)1873 1876).

Particularly preferred esters are glycinate esters and the peptide ester based on β-alanine lysine. These esters are pro drugs which are converted to the camptothecin analog compound by hydrolysis of the ester bond. The esters may be prepared by the method described in U.S. Pat. No. 4,943,579 which is incorporated herein by reference for a more complete description of the process of preparing the esters and for a description of suitable esters formed by the process. The esterification synthon may need to introduced in a protected form, such that the reaction of amine groups is inhibited, followed by removal of the protecting group.

Such protecting groups are well known to those of ordinary skill in the art and are described by Hudkins et al. *Bioorg. Med. Chem. Lett*, 8 (1998)1873 1876).

Specific examples of non limiting compounds include 10,11-difluoromethylenedioxy-20-(S)-camptothecin E-ring ketone; 7-ethyl 10,11-difluoromethylenedioxy-20-(S)-camptothecin E-ring ketone; 7-chloromethyl 10,11-difluoromethylenedioxy-20-(S)-camptothecin E-ring ketone; 7-bromomethyl 10,11-difluoromethylenedioxy-20-(S)-camptothecin E-ring ketone; 7-hydroxymethyl 10,11-difluromethylenedioxy-20-(S)-camptothecin E-ring ketone, 9-nitro 10,11-difluoromethylenedioxy-20-(S)-camptothecin E-ring ketone, 9-amino 10,11-difluoromethylenedioxy-20-(S)-camptothecin E-ring ketone, 7-ethyl-9-nitro 10,11-difluoromethylenedioxy-20-(S)-camptothecin E-ring ketone and 7-ethyl-9-amino 10,11-difluoromethylenedioxy-20-(S)-camptothecin E-ring ketone.

Specific non limiting examples further include the C$_{20}$ amino acid ester of the above identified compounds 10,11-difluoromethylenedioxy-20-O-glycinyl-20-(S)-camptothecin E-ring ketone; 7-ethyl 10,11-difluoromethylenedioxy-20-O-glycinyl-20-(S)-camptothecin E-ring ketone; 7-chloromethyl 10,11-difluoromethylenedioxy-20-O-glycinyl-20-(S)-camptothecin E-ring ketone; 7-bromomethyl 10,11-difluoromethylenedioxy-20-O-glycinyl-20-(S)-camptothecin E-ring ketone; 7-hydroxymethyl 10,11-difluromethylenedioxy-20-O-glycinyl-20-(S)-camptothecin E-ring ketone, 9-nitro 10,11-difluoromethylenedioxy-20-O-glycinyl-20-(S)-camptothecin E-ring ketone, 9-amino 10,11-difluoromethylenedioxy-20-O-glycinyl-20-(S)-camptothecin E-ring ketone, 7-ethyl-9-nitro 10,11-difluoromethylenedioxy-20-O-glycinyl-20-(S)-camptothecin E-ring ketone, 7-ethyl-9-amino 10,11-difluoromethylenedioxy-20-O-glycinyl-20-(S)-camptothecin E-ring ketone, 10,11-difluoromethylenedioxy-20-O-N-methylglycinyl-20-(S)-camptothecin E-ring ketone; 7-ethyl 10,11-difluoromethylenedioxy 20-O-N methylglycinyl-20-(S)-camptothecin E-ring ketone; 7-chloromethyl 10,11-difluoromethylenedioxy 20-O-N methylglycinyl-20-(S)-camptothecin E-ring ketone; 7-bromomethyl 10,11-difluoromethylenedioxy 20-O-N methylglycinyl-20-(S)-camptothecin E-ring ketone; 7-hydroxymethyl 10, 11 difluromethylenedioxy 20-O-N methylglycinyl-20-(S)-camptothecin E-ring ketone, 9-nitro 10,11-difluoromethylenedioxy 20-O-N methylglycinyl-20-(S)-camptothecin E-ring ketone, 9-amino 10,11-difluoromethylenedioxy 20-O-N methylglycinyl-20-(S)-camptothecin E-ring ketone, 7-ethyl-9-nitro 10,11-difluoromethylenedioxy 20-O-N methylglycinyl-20-(S)-camptothecin E-ring ketone, 7-ethyl-9-amino 10,11-difluoromethylenedioxy 20-O-N methylglycinyl-20-(S)-camptothecin E-ring ketone, 10,11-difluoromethylenedioxy 20-O-N,N dimethylglycinyl-20-(S)-camptothecin E-ring ketone; 7-ethyl 10,11-difluoromethylenedioxy 20-O-N,N dimethylglycinyl-20-(S)-camptothecin E-ring ketone; 7-chloromethyl 10,11-difluoromethylenedioxy 20-O-N,N dimethylglycinyl-20-(S)-camptothecin E-ring ketone; 7-bromomethyl 10,11-difluoromethylenedioxy 20-O-N,N dimethylglycinyl-20-(S)-camptothecin E-ring ketone; 7-hydroxymethyl 10,11-difluromethylenedioxy 20-O-N,N dimethylglycinyl-20-(S)-camptothecin E-ring ketone, 9-nitro 10,11-difluoromethylenedioxy 20-O-N,N dimethylglycinyl-20-(S)-camptothecin E-ring ketone, 9-amino 10,11-difluoromethylenedioxy 20-O-N,N dimethylglycinyl-20-(S)-camptothecin E-ring ketone, 7-ethyl-9-nitro 10,11-difluoromethylenedioxy 20-O-N,N dimethylglycinyl-20-(S)-camptothecin E-ring ketone and 7-ethyl-9-amino 10,11-difluoromethylenedioxy 20-O-N,N dimethylglycinyl-20-(S)-camptothecin E-ring ketone.

Additional specific non limiting examples further include 10,11-difluoromethylenedioxy-20-O-β-ala-lys-20-(S)-camptothecin E-ring ketone; 7-ethyl 10,11-difluoromethylenedioxy-20-O-β-ala-lys-20-(S)-camptothecin E-ring ketone; 7-chloromethyl 10,11-difluoromethylenedioxy-20-O-β-ala-lys-20-(S)-camptothecin E-ring ketone; 7-bromomethyl 10,11-difluoromethylenedioxy-20-O-β-ala-lys-20-(S)-camptothecin E-ring ketone; 7-hydroxymethyl 10,11-difluromethylenedioxy-20-O-β-ala-lys-20-(S)-camptothecin E-ring ketone, 9-nitro 10,11-difluoromethylenedioxy-20-O-β-ala-lys-20-(S)-camptothecin E-ring ketone, 9-amino 10,11-difluoromethylenedioxy-20-O-β-ala-lys-20-(S)-camptothecin E-ring ketone, 7-ethyl-9-nitro 10,11-difluoromethylenedioxy-20-O-β-ala-lys-20-(S)-camptothecin E-ring ketone and 7-ethyl-9-amino 10,11-difluoromethylenedioxy-20-O-β-ala-lys-20-(S)-camptothecin E-ring ketone.

Additional specific non limiting examples further include 10,11-difluoromethylenedioxy-20-O-β-ala-20-(S)-camptothecin E-ring ketone; 7-ethyl 10,11-difluoromethylenedioxy-20-O-β-ala-20-(S)-camptothecin E-ring ketone; 7-chloromethyl 10,11-difluoromethylenedioxy-20-O-β-ala-20-(S)-camptothecin E-ring ketone; 7-bromomethyl 10,11-difluoromethylenedioxy-20-O-β-ala-20-(S)-camptothecin E-ring ketone; 7-hydroxymethyl 10,11-difluromethylenedioxy-20-O-β-ala-20-(S)-camptothecin E-ring ketone, 9-nitro 10,11-difluoromethylenedioxy-20-O-β-ala-20-(S)-camptothecin E-ring ketone, 9-amino 10,11-difluoromethylenedioxy-20-O-β-ala-20-(S)-camptothecin E-ring ketone, 7-ethyl-9-nitro 10,11-difluoromethylenedioxy-20-O-β-ala-20-(S) -camptothecin E-ring ketone and 7-ethyl-9-amino 10,11-difluoromethylenedioxy-20-O-β-ala-20-(S)-camptothecin E-ring ketone.

The compounds of the present invention may be prepared by conventional methods known to those of ordinary skill in the art, without undue experimentation.

For example, the claimed compounds may be prepared by condensation of a aminophenylcarbonyl of formula IV or V

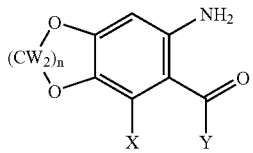

(IV)

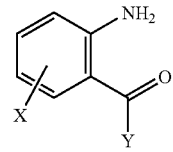

(V)

where X, Y, W and n are as defined for formula I with a tricyclic ketone of formula III

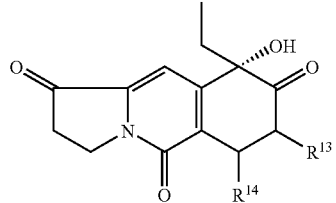

(III)

where $R^{13}$ and $R^{14}$ are defined as for formula I.

The condensation reaction is analogous to the condensation reaction described by Wall et al. U.S. Pat. No. 5,122,526, the relevant portions of which are hereby incorporated by reference.

The synthetic sequence is described with reference to FIG. 1. The 20-desoxy tricyclic analog (1) is treated with an appropriate amine as shown in the example. It is a cyclopentyl amine and the corresponding amide (2) is obtained. On acetylation, 2 is converted to the acetate 3. The next step is a homologation reaction. Other homologation reactions may be carried out by converting 2 to a bromide, etc. The compound 4 is converted to a hydroxy derivative containing one more carbon atom, compound 5. Compound 5 may be brominated to the bromo analog 6. Compound 6 in turn is converted as shown to the tricyclic 20-desoxy ketone 7. Compound 7 may be hydroxylated to the (RS)-20-hydroxy compound 8. Finally, acidic cleavage of the ketal yields the 20(RS)-hydroxy ketone 9 which is the reactant that can be converted now to many camptothecin analogs (as shown in the attached example).

Figure 2:
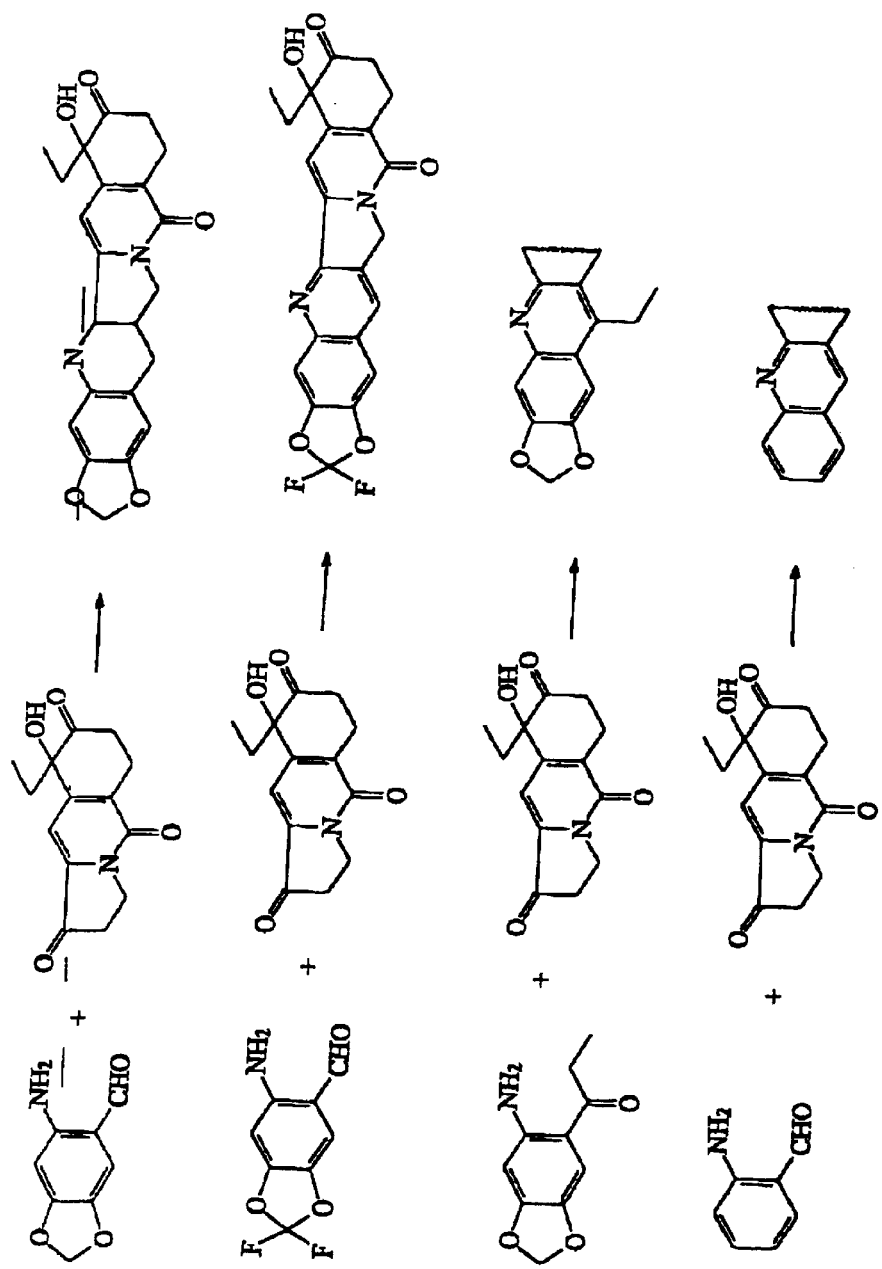
FIG. 2 illustrates a synthetic reaction scheme for preparing compounds according to the present invention.

Additional, non limiting examples of condensation reactions are illustrated in FIG. 2.

Figure 3:
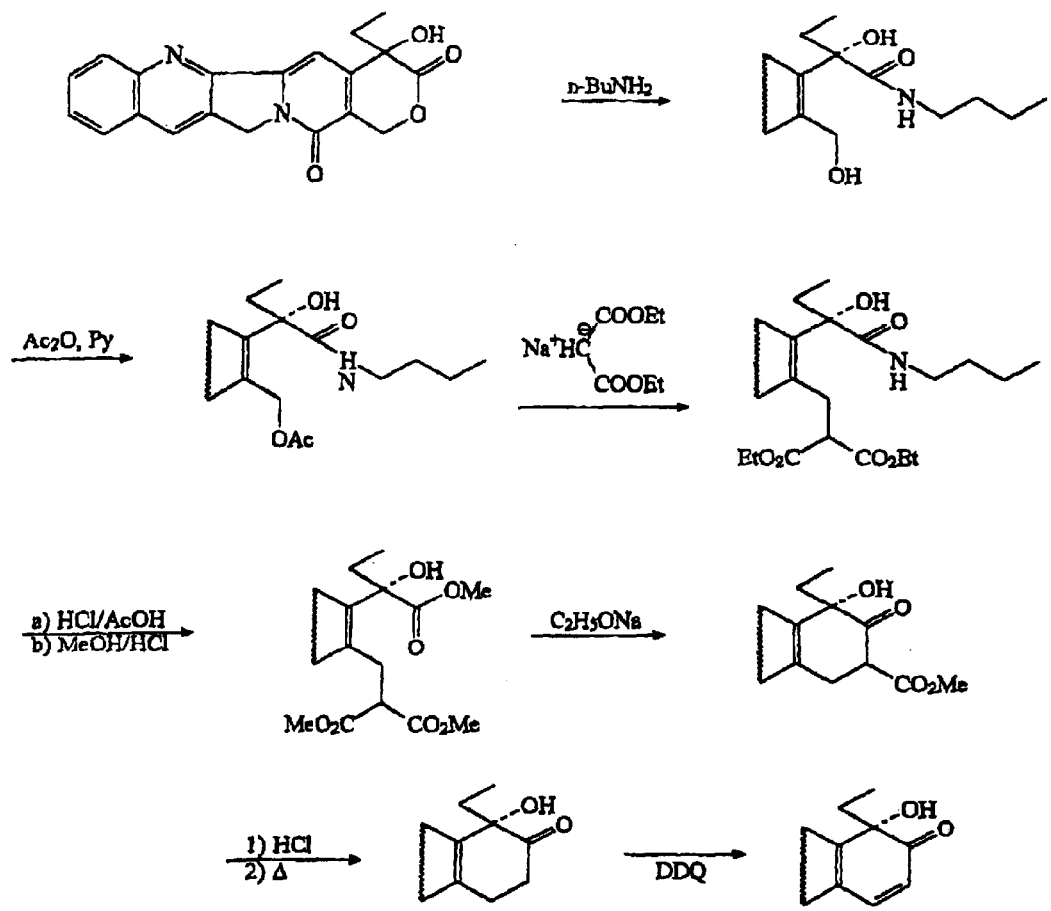
FIG. 3 illustrates a synthetic reaction scheme for preparing compounds according to the present invention.

Alternatively, suitable E-ring ketone compounds may also be prepared from the corresponding compothecin compound bearing an E-ring lactone, illustrated in FIG. 3, by the following reaction sequence:

i) reaction of the E-ring lactone with a primary alkylamine to form an α-hydroxy alkylamide;

ii) activation of a pendant D ring hydroxymethylene group to form a leaving group, such as by formation of an acetate, followed by a displacement reaction with a dialkyl malonate, such as diethylmalonate;

iii) esterification of the alkylamide to an alkyl ester;

iv) cyclization of a D-ring methylene malonate onto the alkyl ester to form the E-ring ketone followed by decarboxylation of an ester group; and v) decarboxylation of the remaining ester group.

In a further embodiment, an α-β E-ring unsaturation may be introduced by conventional methods known to those of ordinary skill in the art, such as by reacion with DDQ.

An alternative procedure for preparing the E-ring ketone from camptothecin is attached and involves a procedure as shown. If the E-ring ketone can be prepared at the very end, a conjugated B ring can be prepared as shown in the very last step. Such a compound might have very interesting properties. It might possibly intercalate with DNA whereas camptothecin does not.

Substitution at the $C_7$ position may be conducted by condensation with the corresponding aldehyde of the $C_7$ substituent. Esterification with an amino acid at $C_{20}$ is possible by conventional methods known to those of ordinary skill in the art. Substitution at $C_9$ with groups such a nitro and amino is also possible in a manner analogous to that described in the literature.

The compounds of the invention having the group —$CH_2$-L at $C_9$ are prepared from known 20(S)-CPT compounds bearing a halogen, for example, a bromine atom, at the $C_9$ position. The halogen atom can be readily converted into the corresponding cyano analog by reaction with CuCN, followed by hydrolysis to form the corresponding carboxy analog. The carboxy analog is reduced to the corresponding hydroxy methyl analog which can be reacted with $Ph_3P$—$CCl_4$ to provide the corresponding chloromethyl analog. The chloromethyl analog can be readily converted to the bromomethyl and iodomethyl analogs using LiBr or LiI. The remaining compounds of the invention are prepared from these compounds by reaction with the corresponding acid chloride, sulfonyl chloride, etc. These reactions are well known to one having ordinary skill in this art.

Compounds in which L is Br or I are readily prepared from the compound in which L is Cl by simple halide exchange employing LiBr or LiI in dimethylformamide (DMF) solution (Larock, R. C., Comprehensive Organic Transformations, VCH Publishers, Inc., p. 337, N.Y. 1989).

Alternatively, the 7-methyl compounds (L is H) can be prepared either by a Friedlander reaction employing the corresponding acetophenone, or by a free radical alkylation reaction (Sawada et al., 1991, Chem. Pharm. Bull., 39:2574). Free radical bromination of 7-methyl substrates can be accomplished by employing N-bromosuccinimide (NBS) in acetic acid (HOAc) under catalysis by benzoyl peroxide to give compounds in which L is Br.

9-Nitro-difluoro-10,11-methylenedioxy-20-(S)-camptothecin may be prepared from difluoro-10,11-methylenedioxy-20-(S)-camptothecin by treatment with $HNO_3$. 9-Amino difluoro-10,11-methylenedioxy-20-(S)-camptothecin may be prepared from 9-nitro difluoro-10,11-methylenedioxy-20-(S)-camptothecin via reduction with $SnCl_2$.

Other compounds which possess oxygen derived leaving groups, such as triflate or tosylate, are prepared from the 7-hydroxymethyl and/or 7-halomethyl compounds. The 7-hydroxymethyl compounds are prepared from the corresponding parent compounds by the hydroxymethylation reaction. (e.g. Sawada et al., 1991, Chem. Pharm. Bull., 39:2574) Treatment of these compounds with readily available sulfonic acid chlorides or anhydrides using known procedures (Stang et al., 1982, Synthesis, 85) provides the highly electrophilic substrates noted above. Alternatively, the compounds described above can be generated from any of the substrates where L is Cl, Br or I by reaction with the silver salt of the corresponding acid (e.g., silver trifluoromethanesulfonate, silver tosylate, etc.) as described generally by Stang et al. and more specifically by Gramstad and Haszeldine (T. Gramstad and R. N. Haszeldine, 1956, J. Chem. Soc., 173).

$C_{20}$ esters may be prepared by esterifying the 20-position hydroxyl group of a camptothecin analog to form an ester containing a water soluble moiety. Generally, the camptothecin analog is initially suspended in methylene chloride or other inert solvent, stirred and cooled. To the cooled mixture is added one equivalent of an acid having the formula HOOC—$CHR^{10}$—$NR^8R^9$ or HOOC—$(CH_2)_m$—$NR^8R^9$, where m is an integer from 1–6, preferably 2–6, and $R^{10}$ is the side chain of one of the naturally occurring α-amino acids. $R^8$ and $R^9$ are, independently, hydrogen or $C_{1-8}$ alkyl. Suitable side chains $R^{10}$ are the side chains of the amino acids glycine, α-alanine, β-alanine, valine, leucine, isoleucine, phenylalanine, tyrosine, tryptophan, leucine, arginine, histidine, aspartate, glutamate, asparagine, glutamine, cysteine and methionine. Particularly preferred esters are glycinate esters. One equivalent of dicyclohexylcarbodiimide (DCC) and a catalytic amount of an amine base, preferably a secondary or tertiary amine, are also added to the mixture, which is then stirred to complete the reaction. Any precipitate which forms is removed by filtration and the product is isolated after removal of the solvent.

The free amine(s) may be converted to an acid addition salt by the addition of a pharmaceutically acceptable acid. Suitable acids include both inorganic and organic acids. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate and stearate salts. The salts may be purified by crystallization from a suitable solvent.

The water soluble 20-hydroxyl esters of the present invention are substantially less toxic than the parent compounds from which the esters are prepared.

The camptothecin analogs are administered in a dose which is effective to inhibit the growth of tumors. As used herein, an effective amount of the camptothecin analog is intended to mean an amount of the compound that will inhibit the growth of tumors, that is, reduce the site of growing tumors relative to a control in which the tumor is not treated with the camptothecin analog. These effective amounts are generally from about 1–60 mg/kg of body weight per week, preferably about 2–20 mg/kg per week.

The compounds of the present invention may be administered as a pharmaceutical composition containing the camptothecin analog and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. For the purpose of oral therapeutic administration, the aforesaid compounds may be incorporated with excipients and used in the form of tablets, gelatine capsules, troches, capsules, elixirs, suspensions, syrups, wafers, chewing gums and the like. Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed. Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono oleate). The aqueous suspension may also contain one or more preservatives such as ethyl or n-propyl p-hydroxybenzoate, one or more coloring agents, one or more flavoring agents and one or more sweetening agents, such as sucrose, aspartame, saccharin, or sucralose.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil in water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil in water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non limiting examples of such materials are cocoa butter and polyethylene glycols.

They may also be administered by intranasal, intraocular, intravaginal, and intrarectal routes including suppositories, insufflation, powders and aerosol formulations.

The compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. No. 4,452,747, U.S. Pat. No. 4,448,765, U.S. Pat. No. 4,837,028, U.S. Pat. No. 4,721,612, U.S. Pat. No. 4,594,241, U.S. Pat. No. 4,302,459 and U.S. Pat. No. 4,186,183. The disclosures of these U.S. patents are incorporated herein by reference. Suitable liposome preparations for use in the present invention are also described in WO-9318749-A1, J-02056431-A and EP-276783-A.

The camptothecin analogs may be used individually to inhibit the growth of tumors. Alternatively, combinations of two or more camptothecin analogs may be used or combinations of one or more camptothecin analogs with one or more known anti tumor compounds. When a camptothecin analog is combined with a conventional anti tumor compound, the camptothecin analog will generally be present in an amount ranging from about 1–99 wt. %, preferably, 5–95 wt. % of the combined amount of camptothecin and conventional anti tumor compound. The pharmaceutical compositions noted above may contain these combinations of compounds together with an acceptable carrier or diluent.

The ester compounds of the invention may be administered to treat leukemia and solid tumors in mammals, including humans. The esters of the present invention are prodrugs which are hydrolyzed to camptothecin analogs demonstrating inhibitory activity on topoisomerase I. The camptothecin analogs formed by hydrolysis of the esters of the invention are also effective in treating leukemia and solid tumors in mammals. Numerous camptothecin analogs have been shown to be effective against leukemia using the standard L1210 leukemia assay (Wall et al. (1993), Journal of Medicinal Chemistry, 36:2689–2700). High activity of camptothecin and camptothecin analogs has also been shown in the P388 leukemia assay (Wall (1983), Medical and Pediatric Oncology, 11:480A–489A). The later reference also provides a correlation between anti leukemia activity as determined by the L1210 and the P388 leukemia assays with efficacy of camptothecin analogs against solid tumors. Compounds reported as active in the leukemia assays also have demonstrated activity in a number of solid tumors including a colon xenograft, a lung xenograft, a Walker sarcoma and a breast xenograft (Wall (1983), Table IV, page 484 A). Recent studies have confirmed the correlation between topoisomerase I inhibitory activity and anti leukemia/anti tumor activity of camptothecin analogs (Giovanella et al. (1989), Science, 246: 1046–1048). The compounds of the present invention are particularly effective in the treatment of colon, lung, breast and ovary solid tumors, brain glioma and leukemia. These compounds may also be used to treat malaria.

Obviously, numerous modifications and variations of the present invention are possible in light of the above teachings. It is therefore to be understood that within the scope of the appended claims, the invention may be practiced otherwise than as specifically described herein.

What is claimed is:

1. A camptothecin analog having the structure:

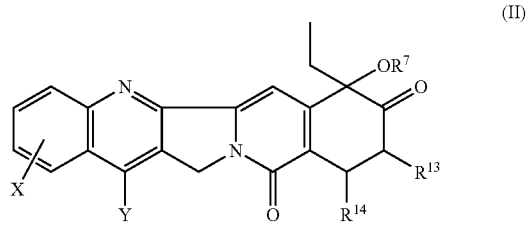

(II)

where

X and Y are each independently SH, S—$C_{1-6}$ alkyl, NH—$C_{1-6}$ alkyl, CHO, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl$)_2$ wherein Z is selected from the group consisting of O, NH and S, and a is an integer of 2 or 3, or —$CH_2$-L, where L is halogen, $^+N_2$, $^+(OR^1)_2$, $^+S(R^1)_2$, $^+N(R^1)_3$, $OC(O)R^1$, $OSO_2R^1$, $OSO_2CF_3$, $OSO_2C_4F_9$, $C_{1-6}$ alkyl-C(=O)—, $C_{4-18}$ aryl-C(=O)—, $C_{1-6}$ alkyl-$SO_2$—, perfluoro $C_{1-6}$ alkyl-$SO_2$— or $C_{4-18}$ aryl-$SO_2$—, (where each $R^1$ independently is $C_{1-6}$ alkyl, $C_{4-18}$ aryl or $C_{4-18}$ Ar$C_{1-6}$ alkyl);

$R^7$ is H; and $R^{13}$ and $R^{14}$ are each H or combine to form a double bond;

and salts thereof.

2. The camptothecin analog of claim 1, wherein Y is —$CH_2$-L.

3. The camptothecin analog of claim 1, wherein L is selected from the group consisting of Cl, Br and I.

4. The camptothecin analog of claim 1, which is selected from the group consisting of 20-R isomers, 20-S isomers and mixtures thereof.

5. The camptothecin analog of claim 4, wherein the analog is the 20-S isomer.

6. The camptothecin analog of claim 4, wherein the analog is the 20-R isomer.

7. The camptothecin analog of claim 4, wherein the analog is an 20-S rich mixture of 20-S and 20-R isomers.

8. The camptothecin analog of claim 4, wherein the analog is a 20-R rich mixture of 20-S and 20-R isomers.

9. The camptothecin analog of claim 4, wherein the analog is a racemic mixture of 20-R and 20-S isomers.

10. A method of treating leukemia or solid tumors comprising administering to a patient in need thereof, a therapeutically effective amount of the camptothecin analog of claim 1.

11. A pharmaceutical composition comprising the camptothecin analog of claim 1 and a pharmaceutically acceptable carrier.

12. A method of preparing the camptothecin analog according to claim 1 comprising:

condensing a compound of formula V

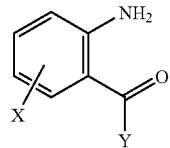
(V)

where X, Y, and W are as defined in claim 1, with a tricyclic ketone of formula III

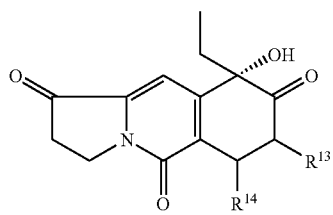
(III)

where $R^{13}$ and $R^{14}$ are as defined in claim 1 to form the camptothecin analog of claim 1.

13. A camptothecin analog having the structure:

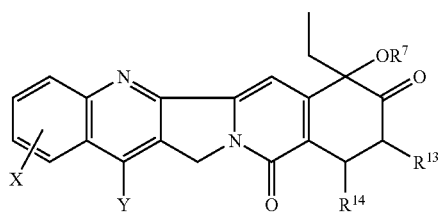
(II)

where

X is $NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, N($C_{1-6}$ alkyl)$_2$, CHO, $C_{1-8}$ alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl)$_2$ wherein Z is selected from the group consisting of O, NH and S, and a is an integer of 2 or 3, or —$CH_2$-L, where L is halogen, $^+N_2$, $^+(OR^1)_2$, $^+S(R^1)_2$, $^+N(R^1)_3$, $OC(O)R^1$, $OSO_2R^1$, $OSO_2CF_3$, $OSO_2C_4F_9$, $C_{1-6}$ alkyl-C(=O)—, $C_{4-18}$ aryl-C(=O)—, $C_{1-6}$ alkyl-$SO_2$—, perfluoro $C_{1-6}$ alkyl-$SO_2$— or $C_{4-18}$ aryl-$SO_2$—, (where each $R^1$ independently is $C_{1-6}$ alkyl, $C_{4-18}$ aryl or $C_{4-18}$ Ar$C_{1-6}$ alkyl); or —$CH_2NR^2R^3$, where (a) $R_2$ and $R_3$ are, independently, hydrogen, $C_{1-6}$ alkyl, $C_{3-7}$ cycloalkyl, $C_{3-7}$ cycloalkyl $C_{1-6}$ alkyl, $C_{2-6}$ alkenyl, hydroxy $C_{1-6}$ alkyl, $C_{1-6}$ alkoxy $C_{1-6}$ $COR^4$ where $R^4$ is hydrogen, $C_{1-6}$ alkyl, perhalo $C_{1-6}$ alkyl, $C_{3-7}$ cycloalkyl, $C_{3-7}$ cycloalkyl-$C_{1-6}$ alkyl, $C_{2-6}$ alkenyl, hydroxyl-$C_{1-6}$ alkyl, $C_{1-6}$-alkoxy, or $C_{1-6}$ alkoxy-$C_{1-6}$ alkyl;

Y is SH, S—$C_{1-6}$ alkyl, NH—$C_{1-6}$ alkyl, —CHO, $N_3$,

—Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl)$_2$ wherein Z is selected from the group consisting of O, NH and S, and a is an integer of 2 or 3, or —$CH_2$-L, where L is halogen, $^+N_2$, $^+(OR)_2$, $^+S(R^1)_2$, $^+N(R^1)_3$, $OC(O)R^1$, $OSO_2R_1$, $OSO_2CF_3$, $OSO_2C_4F_9$, $C_{1-6}$ alkyl-C(=O)—, $C_{4-18}$ aryl-C(=O)—, $C_{1-6}$ alkyl-$SO_2$—, perfluoro $C_{1-6}$ alkyl-$SO_2$— or $C_{4-18}$ aryl-$SO_2$—, (where each $R^1$ independently is $C_{1-6}$ alkyl, $C_{4-18}$ aryl or $C_{4-18}$ Ar$C_{1-6}$ alkyl);

$R^7$ is H; and $R^{13}$ and $R^{14}$ are each H or combine to form a double bond; and salts thereof.

14. A method of treating leukemia or solid tumors comprising administering to a patient in need thereof, a therapeutically effective amount of the camptothecin analog of claim 13.

15. A pharmaceutical composition comprising the camptothecin analog of claim 13 and a pharmaceutically acceptable carrier.

16. A method of preparing the camptothecin analog according to claim 13 comprising:

condensing a compound of formula V

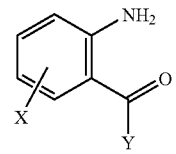
(V)

where X, Y, and W are as defined in claim 13, with a tricyclic ketone of formula III

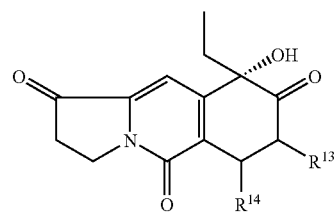
(III)

where $R^{13}$ and $R^{14}$ are as defined in claim 13 to form the camptothecin analog of claim 13.

* * * * *

UNITED STATES PATENT AND TRADEMARK OFFICE
CERTIFICATE OF CORRECTION

PATENT NO.       : 7,071,204 B2
APPLICATION NO.  : 10/608207
DATED            : July 4, 2006
INVENTOR(S)      : Monroe E. Wall et al.

Page 1 of 1

It is certified that error appears in the above-identified patent and that said Letters Patent is hereby corrected as shown below:

Column 5, line 19, "attached form a", should read --attached from a--
         line 65, "to introduced", should read --to be introduced--

Column 8, line 67, "such a", should read --such as--

Column 14, line 54, "an 20-S", should read --a 20-S--

Column 16, line 13, "$^+(OR)_2$", should read --$^+(OR^1)_2$--
          line 14, "$OSO_2R_1$", should read --$OSO_2R^1$--

Signed and Sealed this

Tenth Day of April, 2007

JON W. DUDAS
*Director of the United States Patent and Trademark Office*